United States Patent
Chishti et al.

(10) Patent No.: US 8,326,647 B2
(45) Date of Patent: Dec. 4, 2012

(54) METHOD AND SYSTEM FOR DISTRIBUTING PATIENT REFERRALS

(75) Inventors: Muhammad Chishti, Sunnyvale, CA (US); Kenneth Vargha, San Jose, CA (US); Joe Breeland, Austin, TX (US)

(73) Assignee: Align Technology, Inc., San Jose, CA (US)

( * ) Notice: Subject to any disclaimer, the term of this patent is extended or adjusted under 35 U.S.C. 154(b) by 468 days.

(21) Appl. No.: 12/534,790

(22) Filed: Aug. 3, 2009

(65) Prior Publication Data
US 2009/0292556 A1   Nov. 26, 2009

Related U.S. Application Data

(62) Division of application No. 09/756,885, filed on Jan. 9, 2001, now Pat. No. 7,580,846.

(51) Int. Cl.
*G06Q 10/00* (2012.01)
(52) U.S. Cl. .................................. 705/2; 705/3
(58) Field of Classification Search .................... 705/2, 3
See application file for complete search history.

(56) References Cited

U.S. PATENT DOCUMENTS

| | | | |
|---|---|---|---|
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |

(Continued)

FOREIGN PATENT DOCUMENTS

AU   3031677   5/1979

(Continued)

OTHER PUBLICATIONS

Alcaniz, et al., "An Advanced System for the Simulation and Planning of Orthodontic Treatments," Karl Heinz Hohne and Ron Kikinis (eds.), *Visualization in Biomedical Computing, 4th Int'. Conf., VBC '96*, Hamburg, Germany, Sep. 22-25, 1996, Springer-Verlag, pp. 511-520.

(Continued)

*Primary Examiner* — Lena Najarian
(74) *Attorney, Agent, or Firm* — Wilson Sonsini Goodrich & Rosati (57) ABSTRACT

Practitioners are certified to perform a medical procedure, such as an orthodontic procedure. Certified practitioners are maintained in a referral directory and classified within tiers based on criteria such as the number of procedures that they have performed. Inquiries are solicited from prospective patients, and referral lists are provided to those patients who request them. The referral lists are obtained from the referral directory with doctors from higher tiers who have performed more procedures receiving preferential inclusion on the referral lists.

26 Claims, 3 Drawing Sheets

U.S. PATENT DOCUMENTS

| | | |
|---|---|---|
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,225,976 A * | 7/1993 | Tawil ................................ 705/2 |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,014,629 A * | 1/2000 | DeBruin-Ashton ............... 705/2 |
| 6,015,289 A | 1/2000 | Andreiko et al. |
| 6,035,276 A | 3/2000 | Newman et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,210,162 B1 | 4/2001 | Chishti et al. |
| 6,217,325 B1 | 4/2001 | Chishti et al. |
| 6,217,334 B1 | 4/2001 | Hultgren |
| 6,227,850 B1 | 5/2001 | Chishti et al. |
| 6,227,851 B1 | 5/2001 | Chishti et al. |
| 6,244,861 B1 | 6/2001 | Andreiko et al. |
| 6,299,440 B1 | 10/2001 | Phan et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,371,761 B1 | 4/2002 | Cheang et al. |
| 6,382,975 B1 | 5/2002 | Poirier |
| 6,385,620 B1 * | 5/2002 | Kurzius et al. ....................... 1/1 |
| 6,398,548 B1 | 6/2002 | Muhammad et al. |
| 6,402,707 B1 | 6/2002 | Ernst |
| 6,406,292 B1 | 6/2002 | Chishti et al. |
| 6,409,504 B1 | 6/2002 | Jones et al. |
| 6,450,807 B1 | 9/2002 | Chishti et al. |
| 6,463,344 B1 | 10/2002 | Pavloskaia et al. |
| 6,471,511 B1 | 10/2002 | Chishti et al. |
| 6,482,298 B1 | 11/2002 | Bhatnagar |
| 6,514,074 B1 | 2/2003 | Chishti et al. |
| 6,524,101 B1 | 2/2003 | Phan et al. |
| 6,554,611 B2 | 4/2003 | Chishti et al. |
| 6,571,214 B2 | 5/2003 | Newman et al. |
| 6,572,372 B1 | 6/2003 | Phan et al. |
| 6,621,491 B1 | 9/2003 | Baumrind et al. |
| 6,626,725 B1 | 9/2003 | Bell |
| 6,629,840 B2 | 10/2003 | Chishti et al. |
| 6,633,789 B1 | 10/2003 | Nikolskiy et al. |
| 6,705,863 B2 | 3/2004 | Phan et al. |
| 6,722,880 B2 | 4/2004 | Chishti et al. |
| 7,063,532 B1 | 6/2006 | Jones et al. |
| 7,092,784 B1 | 8/2006 | Simkins |
| 7,245,977 B1 | 7/2007 | Simkins |
| 7,383,198 B1 | 6/2008 | Sepe |
| 7,490,048 B2 | 2/2009 | Joao |
| 7,761,308 B2 | 7/2010 | Falchuk et al. |
| 7,802,987 B1 | 9/2010 | Phan |
| 2001/0034639 A1 | 10/2001 | Jacoby et al. |
| 2002/0006597 A1 | 1/2002 | Andreiko et al. |
| 2002/0069085 A1 | 6/2002 | Engel et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer |
| 2004/0128010 A1 | 7/2004 | Pavlovskaia et al. |
| 2005/0055118 A1 | 3/2005 | Nikolskiy et al. |

FOREIGN PATENT DOCUMENTS

| | | |
|---|---|---|
| AU | 517102 | 7/1981 |
| AU | 5598894 | 6/1994 |
| CA | 1121955 | 4/1982 |
| DE | 2749802 | 5/1978 |
| DE | 69327661 | 7/2000 |
| EP | 0091876 | 10/1983 |
| EP | 0299490 | 1/1989 |
| EP | 0376873 | 7/1990 |
| EP | 0490848 | 6/1992 |
| EP | 0541500 | 5/1993 |
| EP | 0667753 | 8/1995 |
| EP | 0731673 | 9/1996 |
| EP | 0774933 | 5/1997 |
| ES | 463897 | 1/1980 |
| FR | 2369828 | 6/1978 |

| | | |
|---|---|---|
| FR | 2652256 | 3/1991 |
| GB | 1550777 | 8/1979 |
| JP | 53-058191 | 5/1978 |
| JP | 04-028359 | 1/1992 |
| JP | 08-508174 | 9/1996 |
| WO | 90/08512 | 8/1990 |
| WO | 91/04713 | 4/1991 |
| WO | 94/10935 | 5/1994 |
| WO | 98/32394 | 7/1998 |
| WO | 98/44865 | 10/1998 |
| WO | 98/58596 | 12/1998 |

OTHER PUBLICATIONS

"Important Tip About Wearing the Red White & Blue Active Clear Retainer System," Allesee Orthodontic Appliances-Pro Lab, 1 page (no date given).
"Inside the ADA," *JADA*, 118:286-294 (Mar. 1989).
"The Choice Is Clear: Red, White & Blue ... The Simple, Affordable, No-Braces Treatment," Allesee Orthodontic Appliances—Pro Lab product information for doctors, <http://ormco.com/aoa/appliancesservices/RWB/doctorhtml>, 5 pages (May 19, 2003).
"The Choice is Clear: Red, White & Blue ... The Simple, Affordable, No-Braces Treatment," Allesee Orthodontic Appliances—Pro Lab product information for patients, <http://ormco.com/aoa/appliancesservices/RWB/patients.html>, 2 pages (May 19, 2003).
"The Choice Is Clear: Red, White & Blue ... The Simple, Affordable, No-Braces Treatment," Allesee Orthodontic Appliances—Pro Lab product information, 6 pages (2003).
"The Red, White & Blue Way to Improve Your Smile!" Allesee Orthodontic Appliances—Pro Lab product information for patients, 2 pages (no date given).
"You May Be a Candidate for This Invisible No-Braces Treatment," Allesee Orthodontic Appliances—Pro Lab product information for patients, 2 pages (no date given).
Alexander et al., "The DigiGraph Work Station Part 2 Clinical Management," *JCO*, pp. 402-407 (Jul. 1990).
Altschuler et al., "Measuring Surfaces Space-Coded by a Laser-Projected Dot Matrix," *SPIE Imaging Applications for Automated Industrial Inspection and Assembly*, vol. 182, p. 187-191 (1979).
Altschuler et al., "Analysis of 3-D Data for Comparative 3-D Serial Growth Pattern Studies of Oral-Facial Structures, "AADR Abstracts, Program and Abstracts of Papers, 57th General Session, IADR Annual Session, Mar. 29, 1979—Apr. 1, 1979, New Orleans Marriot, *Journal of Dental Research*, vol. 58, Jan. 1979, Special Issue A, p. 221.
Altschuler et al., "Laser Electro-Optic System for Rapid Three-Dimensional (3D) Topographic Mapping of Surfaces," *Optical Engineering*, 20(6):953-961 (1981).
Altschuler, "3D Mapping of Maxillo-Facial Prosthesis," AADR Abstract #607, 2 pages total, (1980).
American Association for Dental Research, Summary of Activities, Mar. 20-23, 1980, Los Angeles, CA, p. 195.
Andersson et al., "Clinical Results with Titanium Crowns Fabricated with Machine Duplication and Spark Erosion," *Acta. Odontol. Scand.*, 47:279-286 (1989).
Andrews, *The Six Keys to Optimal Occlusion Straight Wire*, Chapter 3, pp. 13-24 (no date given).
Anonymous, "Health Pages: The Voice of the Healthcare Consumer." [online], Oct. 1999 [retrieved on Mar. 28, 2002]. Retrieved from the Internet: <URL: http://thehealthpages.com>.
Bartels, et al., *An Introduction to Splines for Use in Computer Graphics and Geometric Modeling*, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, *SPIE*, vol. 166, pp. 112-123.
Baumrind et al., "Mapping the Skull in 3-D," reprinted from *J. Calif. Dent. Assoc.*, 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," *Semin. in Orthod.*, 7(4):223-232 (Dec. 2001).
Begole et aL, "A Computer System for the Analysis of Dental Casts," *The Angle Orthod.*, 51(3):253-259 (Jul. 1981).
Bernard et al.,"Computerized Diagnosis in Orthodontics for Epidemiological Studies: A Progress Report," Abstract, *J. Dental Res. Special Issue*, vol. 67, p. 169, paper presented at International Association for Dental Research 66th General Session, Mar. 9-13, 1988, Montreal, Canada.
Bhatia et al., "A Computer-Aided Design for Orthognathic Surgery," *Br. J. Oral Maxillofac. Surg.*, 22:237-253 (1984).
Biggerstaff et al., "Computerized Analysis of Occlusion in the Postcanine Dentition," *Am. J. Orthod.*, 61(3): 245-254 (Mar. 1972).
Biggerstaff, "Computerized Diagnostic Setups and Simulations," *Angle Orthod.*, 40(1):28-36 (Jan. 1970).
Biostar Opeation & Training Manual. Great Lakes Orthodontics, Ltd. 199 Fire Tower Drive, Tonawanda, New York. 14150-5890. 20 pages total (no date given).
Blu, et al., "Linear interpolation revitalized", *IEEE Trans. Image Proc.*, 13(5):710-719 (May 2004).
Bourke, "Coordinate System Transformation," (Jun. 1996), p. 1, retrieved from the Internet Nov. 5, 2004, URL <http://astronomy.swin.edu.au/~pbourke/projection/coords>.
Boyd et al., "Three Dimensional Diagnosis and Orthodontic Treatment of Complex Malocclusions With the Invisalign Appliance," *Semin. Orthod.*, 7(4):274-293 (Dec. 2001).
Brandestini et al., "Computer Machined Ceramic Inlays: In Vitro Marginal Adaptation," *J. Dent. Res. Special Issue*, Abstracts, vol. 64, p. 208 (1985).
Brook et al., "An Image Analysis System for the Determination of Tooth Dimensions from Study Casts: Comparison with Manual Measurements of Mesio-distal Diameter," *J. Dent. Res.*, 65(3):428-431 (Mar. 1986).
Burstone (interview), "Dr. Charles J. Burstone on The Uses of the Computer in Orthodontic Practice (Part 1)," *J. Clin. Orthod.*, 13(7):442-453 (Jul. 1979).
Burstone (interview), "Dr. Charles J. Burstone on The Uses of the Computer in Orthodontic Practice (Part 2)," *J. Clin. Orthod.*, 13(8):539-551 (Aug. 1979).
Burstone et al., Precision Adjustment of the Transpalatal Lingual Arch: Computer Arch Form Predetermination, *Am, Journal of Orthodontics*, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," *JCO*, pp. 360-367 (Jun. 1990).
Chafetz et al., "Subsidence of the Femoral Prosthesis, A Stereophotogrammetric Evaluation," *Clin. Orthop. Relat. Res.*, No. 201, pp. 60-67 (Dec. 1985).
Chiappone, (1980). Constructing the Gnathologic Setup and Positioner, *J. Clin. Orthod*, vol. 14, pp. 121-133.
Cottingham, (1969). Gnathologic Clear Plastic Positioner, *Am. J. Orthod*, vol. 55, pp. 23-31.
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, *Canadian Dental Journal*, vol. 54(9), pp. 661-666 (1988).
Crawford, "CAD/CAM in the Dental Office: Does It Work?", *Canadian Dental Journal*, vol. 57, No. 2, pp. 121-123 (Feb. 1991).
Crooks, "CAD/CAM Comes to USC," *USC Dentistry*, pp. 14-17 (Spring 1990).
Cureton, Correcting Malaligned Mandibular Incisors with Removable Retainers, *J. Clin. Orthod*, vol. 30, No. 7 (1996) pp. 390-395.
Curry et al., "Integrated Three-Dimensional Craniofacial Mapping at the Craniofacial Research Instrumentation Laboratory/University of the Pacific," *Semin. Orthod.*, 7(4):258-265 (Dec. 2001).

Cutting et al., "Three-Dimensional Computer-Assisted Design of Craniofacial Surgical Procedures: Optimization and Interaction with Cephalometric and CT-Based Models," *Plast. Reconstr. Surg.*, 77(6):877-885 (Jun. 1986).

DCS Dental AG, "The CAD/CAM 'DCS Titan System' for Production of Crowns/Bridges," DSC Production AG, pp. 1-7 (Jan. 1992).

Definition for "Gingiva," Dictionary.com, pp. 1-3, retrieved from the Internet on Nov. 5, 2004, URL <http://reference.com/search/search?q=gingiva>.

Defranco et al., "Three-Dimensional Large Displacement Analysis of Orthodontic Appliances," *J. Biomechanics*, 9:793-801 (1976).

Dental Institute University of Zurich Switzerland, Program for International Symposium on Computer Restorations: State of the Art of the CEREC-Method, May 1991, 2 pages total.

Dentrac Corporation, Dentrac document, pp. 4-13 (no date given).

Dent-X posted on Sep. 24, 1998 at <http://www.dent-x.com/DentSim.htm>, 6 pages.

Doyle, "Digital Dentistry," *Computer Graphics World*, pp. 50-52, 54 (Oct. 2000).

DuraClear™ product information, Allesee Orthodontic Appliances—Pro Lab, 1 page (no date given).

Duret et al, "CAD-CAM in Dentistry," *J. Am. Dent. Assoc.*, 117:715-720 (Nov. 1988).

Duret et al., "CAD/CAM Imaging in Dentistry," *Curr. Opin. Dent.*, 1:150-154 (1991).

Duret, "The Dental CAD/CAM, General Description of the Project," *Hennson International Product Brochure*, 18 pages total, Jan. 1986.

Duret,"Vers Une Prosthese Informatisee," (English translation attached), *Tonus*, vol. 75, pp. 55-57 (Nov. 15, 1985).

Economides, "The Microcomputer in the Orthodontic Office," *JCO*, pp. 767-772 (Nov. 1979).

Elsasser, Some Observations on the History and Uses of the Kesling Positioner, *Am. J. Orthod.* (1950) 36:368-374.

English translation of Japanese Laid-Open Publication No. 63-11148 to inventor T. Ozukuri (Laid-Open on Jan. 18, 1998) pp. 1-7.

Faber et al., "Computerized Interactive Orthodontic Treatment Planning," *Am. J. Orthod.*, 73(1):36-46 (Jan. 1978).

Felton et al., "A Computerized Analysis of the Shape and Stability of Mandibular Arch Form," *Am. J. Orthod. Dentofacial Orthop.*, 92(6):478-483 (Dec. 1987).

Friede et al., "Accuracy of Cephalometric Prediction in Orthognathic Surgery," Abstract of Papers, *J. Dent. Res.*, 70:754-760 (1987).

Fütterling et al., "Automated Finite Element Modeling of a Human Mandible with Dental Implants," WSCG '98—Conference Program, retrieved from the Internet: <http://wscg.zcu.cz/wscg98/papers98/Strasser_98.pdf>, 8 pages.

Gao et al., "3-D element Generation for Multi-Connected Complex Dental and Mandibular Structure," Proc. Int'l. Workshop on Medical Imaging and Augmented Reality, pp. 267-271 (Jun. 12, 2001).

Gim-Alldent Deutschland, "Das DUX System: Die Technik," 2 pages total (no date given).

Gottlieb et al., "JCO Interviews Dr. James A. McNamura, Jr., on the Frankel Appliance: Part 2: Clinical Management, "*J. Clin. Orthod.*, 16(6):390-407 (Jun. 1982).

Grayson, "New Methods for Three Dimensional Analysis of Craniofacial Deformity, Symposium: Computerized Facial Imaging in Oral and Maxiiofacial Surgery," *AAOMS*, 3 pages total, (Sep. 13, 1990).

Guess et al., "Computer Treatment Estimates in Orthodontics and Orthognathic Surgery," *JCO*, pp. 262-228 (Apr. 1989).

Heaven et al., "Computer-Based Image Analysis of Artificial Root Surface Caries," Abstracts of Papers, *J. Dent. Res.*, 70:528 (Apr. 17-21, 1991).

Highbeam Research, "Simulating Stress Put on Jaw," Tooling & Production [online], Nov. 1996, pp. 1-2, retrieved from the Internet on Nov. 5, 2004, URL <http://static.highbeam.com/t/toolingamp-production/november011996/simulatingstressputonja...>.

Hikage, "Integrated Orthodontic Management System for Virtual Three-Dimensional Computer Graphic Simulation and Optical Video Image Database for Diagnosis and Treatment Planning", *Journal of Japan Orthodontic Society*, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), *Informatbnen*, pp. 375-396 (Mar. 1991).

Hojjatie et al., "Three-Dimensional Finite Element Analysis of Glass-Ceramic Dental Crowns," *J. Biomech.*, 23(11):1157-1166 (1990).

Huckins, "CAD-CAM Generated Mandibular Model Prototype from MRI Data," *AAOMS*, p. 96 (1999).

"JCO Interviews, Craig Andreiko , DDS, MS on the Elan and Orthos Systems," *JCO*, pp. 459-468 (Aug. 1994).

"JCO Interviews, Dr. Homer W. Phillips on Computers in Orthodontic Practice, Part 2," *JCO*, pp. 819-831 (Dec. 1983).

Jerrold, "The Problem, Electronic Data Transmission and the Law," *AJO-DO*, pp. 478-479 (Apr. 1988).

Jones et al., "An Assessment of the Fit of a Parabolic Curve to Pre- and Post-Treatment Dental Arches," *Br. J. Orthod.*, 16:85-93 (1989).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case Reports, J. Nihon University School of Dentistry (1982) 24(1):1-27.

Kanazawa et al., "Three-Dimensional Measurements of the Occlusal Surfaces of Upper Molars in a Dutch Population," *J. Dent Res.*, 63(11):1298-1301 (Nov. 1984).

Kochanek, "Interpolating Splines with Local Tension, Continuity and Bias Control," *Computer Graphics*, 18(3):33-41 (Jul. 1984).

Kesling et al., The Philosophy of the Tooth Positioning Appliance, *American Journal of Orthodontics and Oral Surgery* (1945) 31:297-304.

Kesling, Coordinating the Predetermined Pattern and Tooth Positioner with Conventional Treatment, *Am. J. Orthod. Oral Surg.* (1946) 32:285-293.

Kleeman et al., The Speed Positioner, *J. Clin. Orthod.* (1996) 30:673-680.

Kunii et al., "Articulation Simulation for an Intelligent Dental Care System," *Displays* 15:181-188 (1994).

Kuroda et al., Three-Dimensional Dental Cast Analyzing System Using Laser Scanning, *Am. J. Orthod. Dentofac. Orthop.* (1996) 110:365-369.

Laurendeau, et al., "A Computer-Vision Technique for the Acquisition and Processing of 3-D Profiles of Dental Imprints: An Application in Orthodontics," *IEEE Transactions on Medical Imaging*, 10(3):453-461 (Sep. 1991).

Leinfelder, et al., "A New Method for Generating Ceramic Restorations: a CAD-CAM System," *J. Am. Dent. Assoc.*, 118(6):703-707 (Jun. 1989).

Manetti, et al., "Computer-Aided Cefalometry and New Mechanics in Orthodontics," (Article Summary in English, article in German), *Fortschr. Kieferorthop.* 44, 370-376 (Nr. 5), 1983.

McCann, "Inside the ADA," *J. Amer. Dent. Assoc.*, 118:286-294 (Mar. 1989).

McNamara et al., "Invisible Retainers," *J. Clin. Orthod.*, pp. 570-578 (Aug. 1985).

McNamara et al., *Orthodontic and Orthopedic Treatment in the Mixed Dentition*, Needham Press, pp. 347-353 (Jan. 1993).

Moermann et al., "Computer Machined Adhesive Porcelain Inlays: Margin Adaptation after Fatigue Stress," IADR Abstract 339, *J. Dent. Res.*, 66(a):763 (1987).

Moles, "Correcting Mild Malalignments—As Easy As One, Two, Three," *AOA/Pro Corner*, vol. 11, No. 1, 2 pages (2002).

Mörmann et al., "Marginale Adaptation von adhäsuven Porzellaninlays in vitro," Separatdruck aus: Schweiz. Mschr. Zahnmed. 95: 1118-1129, 1985.

Nahoum, "The Vacuum Formed Dental Contour Appliance," *N. Y. State Dent. J.*, 30(9):385-390 (Nov. 1964).

Nash, "CEREC CAD/CAM Inlays: Aesthetics and Durability in a Single Appointment," *Dent. Today*, 9(8):20, 22-23 (Oct. 1990).

Nishiyama et al., "A New Construction of Tooth Repositioner by LTV Vinyl Silicone Rubber," *J. Nihon Univ. Sch. Dent.*, 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," *Dentist*, 3 pages total, Jan./Feb. 1989.

Pinkham, "Inventor's CAD/CAM May Transform Dentistry," *Dentist*, 3 pages total, Sep. 1990.

Ponitz, "Invisible Retainers," *Am. J. Orthod.*, 59(3):266-272 (Mar. 1971).

Procera Research Projects, "PROCERA Research Projects 1993—Abstract Collection," pp. 3-28 (1993).

Proffit et al., *Contemporary Orthodontics*, (Second Ed.), Chapter 15, Mosby Inc., pp. 470-533 (Oct. 1993).

Raintree Essix & ARS Materials, Inc., Raintree Essix, Technical Magazine Table of contents and Essix Appliances, <httpz;// www.essix.com/magazine/default.html> Aug. 13, 1997, 7 pages.

Redmond et al., "Clinical Implications of Digital Orthodontics," *Am. J. Orthod. Dentofacial Orthop.*, 117(2):240-242 (2000).

Rekow et al., "CAD/CAM for Dental Restorations—Some of the Curious Challenges," *IEEE Trans. Biomed. Eng.*, 38(4):344-345 (Apr. 1991).

Rekow et al., "Comparison of Three Data Acquisition Techniques for 3-D Tooth Surface Mapping," *Annual International Conference of the IEEE Engineering in Medicine and Biology Society*, 13(1):344-345 (1991).

Rekow, "A Review of the Developments in Dental CAD/CAM Systems," (contains references to Japanese efforts and content of the papers of particular interest to the clinician are indicated with a one-line summary of their content in the bibliography), *Curr. Opin. Dent.*, 2:25-33 (Jun. 1992).

Rekow, "CAD/CAM in Dentistry: A Historical Perspective and View of the Future," *J. Can. Dent. Assoc.*, 58(4):283, 287-288 (Apr. 1992).

Rekow, "Computer-Aided Design and Manufacturing in Dentistry: A Review of the State of the Art," *J. Prosthet. Dent.*, 58(4):512-516 (Oct. 1987).

Rekow, "Dental CAD-CAM Systems: What is the State of the Art?", *J. Amer. Dent. Assoc.*, 122:43-48 (1991).

Rekow, "Feasibility of an Automated System for Production of Dental Restorations, Ph.D. Thesis," Univ. of Minnesota, 244 pages total, Nov. 1988.

Richmond et al., "The Development of the PAR Index (Peer Assessment Rating): Reliability and Validity," *Eur. J. Orthod.*, 14:125-139 (1992).

Richmond et al., "The Development of a 3D Cast Analysis System," *Br. J. Orthod.*, 13(1):53-54 (Jan. 1986).

Richmond, "Recording the Dental Cast in Three Dimensions," *Am. J. Orthod. Dentofacial Orthop.*, 92(3):199-206 (Sep. 1987).

Rudge, "Dental Arch Analysis: Arch Form, A Review of the Literature," *Eur. J. Orthod.*, 3(4):279-284 (1981).

Sakuda et al., "Integrated Information-Processing System in Clinical Orthodontics: An Approach with Use of a Computer Network System," *Am. J. Orthod. Dentofacial Orthop.*, 101(3): 210-220 (Mar. 1992).

Schellhas et al., "Three-Dimensional Computed Tomography in Maxillofacial Surgical Planning," *Arch. Otolamgol. Head Neck Surg.*, 114:438-442 (Apr. 1988).

Schroeder et al., Eds. *The Visual Toolkit*, Prentice Hall PTR, New Jersey (1998) Chapters 6, 8 & 9, (pp. 153-210,309-354, and 355-428, respectively).

Shilliday, (1971). Minimizing finishing problems with the mini-positioner, *Am. J. Orthod.* 59:596-599.

Siemens, "CEREC—Computer-Reconstruction," High Tech in der Zahnmedizin, 14 pages total (no date given).

Sinclair, "The Readers' Corner," *J. Clin. Orthod.*, 26(6):369-372 (Jun. 1992).

Sirona Dental Systems GmbH, *CEREC 3D, Manuel utiiisateur*, Version 2.0X (in French), 2003,114 pages total.

Stoll et al., "Computer-aided Technologies in Dentistry," (article summary in English, article in German), *Dtsch Zahna'rztl Z* 45, pp. 314-322 (1990).

Sturman, "Interactive Keyframe Animation of 3-D Articulated Models," Proceedings Graphics Interface '84, May-Jun. 1984, pp. 35-40.

Truax L., "Truax Clasp-Less(TM) Appliance System," *Funct. Orthod.*, 9(5):22-4, 26-8 (Sep.-Oct. 1992).

Tru-Tain Orthodontic & Dental Supplies, Product Brochure, Rochester, Minnesota 55902, 16 pages total (no date given).

U.S. Department of Commerce, National Technical Information Service, "Automated Crown Replication Using Solid Photography SM," Solid Photography Inc., Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., "Three-Dimensional Analysis of Dental Casts by Means of the Optocom," *J. Dent. Res.*, p. 1100 (Jul.-Aug. 1972).

Van Der Linden, "A New Method to Determine Tooth Positions and Dental Arch Dimensions," *J. Dent. Res.*, 51(4):1104 (Jul.-Aug. 1972).

Van Der Zel, "Ceramic-Fused-to-Metal Restorations with a New CAD/CAM System," *Quintessence Int.*, 24(11):769-778 (1993).

Varady et al., "Reverse Engineering of Geometric Models—An Introduction," *Computer-Aided Design*, 29(4):255-268,1997.

Verstreken et al., "An Image-Guided Planning System for Endosseous Oral Implants," *IEEE Trans. Med. Imaging*, 17(5):842-852 (Oct. 1998).

Warunek et al., Physical and Mechanical Properties of Elastomers in Orthodonic Positioners, *Am J. Orthod. Dentofac. Orthop*, vol. 95, No. 5, (May 1989) pp. 399-400.

Warunek et.al., Clinical Use of Silicone Elastomer Applicances, *JCO* (1989) XXIII(10):694-700.

Wells, Application of the Positioner Appliance in Orthodontic Treatment, *Am. J. Orthodont.* (1970) 58:351-366.

Williams, "Dentistry and CAD/CAM: Another French Revolution," *J. Dent. Practice Admin.*, pp. 2-5 (Jan./Mar. 1987).

Williams, "The Switzerland and Minnesota Developments in CAD/CAM," *J. Dent. Practice Admin.*, pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL <http://wscg.zcu.cz/wscg98/wscg98.h>.

Xia et al., "Three-Dimensional Virtual-Reality Surgical Planning and Soft-Tissue Prediction for Orthognathic Surgery," *IEEE Trans. Inf. Technol. Biomed.*, 5(2):97-107 (Jun. 2001).

Yamamoto et al., "Optical Measurement of Dental Cast Profile and Application to Analysis of Three-Dimensional Tooth Movement in Orthodontics," *Front. Med. Biol. Eng.*, 1(2):119-130 (1988).

Yamamoto et al., "Three-Dimensional Measurement of Dental Cast Profiles and Its Applications to Orthodontics," *Conf. Proc. IEEE Eng. Med. Biol. Soc.*, 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," *Nippon Dental Review*, 452:61-74 (Jun. 1980).

Yoshii, "Research on a New Orthodontic Appliance: The Dynamic Positioner (D.P.); II. The D.P. Manufacturing Procedure and Clinical Applications," *Nippon Dental Review*, 454:107-130 (Aug. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," *Nippon Dental Review*, 458:112-129 (Dec. 1980).

Yoshii, "Research on a New Orthodontic Appliance: The Dynamic Positioner (D.P.); III. The General Concept of the D.P. Method and Its Thereutic Effect, Part 1, Dental and Functional Reversed Occlusion Case Reports," *Nippon Dental Review*, 457:146-164 (Nov. 1980).

\* cited by examiner

1. Dr. A. Loophole
   Address
   Phone No.

2. Dr. B. Twillie
   Address
   Phone No.

3. Dr. C. Sousé
   Address
   Phone No.

FIG. 3

METHOD AND SYSTEM FOR DISTRIBUTING PATIENT REFERRALS

CROSS-REFERENCES TO RELATED APPLICATIONS

The present invention is a divisional application of U.S. Application Ser. No. 09/756,885, filed on Jan 9, 2001 the entire content of which is incorporated herein by reference.

BACKGROUND OF THE INVENTION

The present invention relates generally to business methods and more particularly to methods for referring practitioners certified to perform certain procedures to prospective patients.

Quality healthcare is a matter of overriding concern to the U.S. and worldwide populations. New medical and dental devices and procedures have been and will continue to contribute significantly to improvements in the quality of healthcare in the U.S. and abroad. Each new procedure is unique, and many new procedures and technologies require a learning period for the practitioner. For many such technologies, the creator of the technology, typically a company having a proprietary interest in the technology, will play a significant role in developing and disseminating the technology to practitioners. Frequently, the company will offer training to licensed doctors, dentists, and other health professionals, and will make "certification" resulting from such training a prerequisite to the dispensing and distribution of devices required to perform the new procedures.

Of particular interest to the present application, Align Technology, Inc., Santa Clara, Calif., has recently developed an orthodontic treatment system under the Invisalign® trade name. The Invisalign® System is dispensed to patients only by orthodontic practitioners who have been certified by Align to perform the new orthodontic procedure.

Align Technology, Inc., maintains an advertising campaign intended to inform patients of the availability and advantages of orthodontic treatment using the Invisalign® System. As part of the advertising campaign, potential patients are invited to contact Align by telephone or over the internet. As a result of such solicitation, Align receives many patient inquiries and is in a position to refer patients to individual practitioners.

In referring potential patients to individual practitioners, several objectives must be met. First, the referral process should be inclusive and assure that at least many of the practitioners who have been certified will receive referrals to assist them in developing their practices. It is also important, however, to avoid over loading relatively inexperienced practitioners who might otherwise benefit from additional time and patient experience to develop their skills in the new procedures. Finally, it would be advantageous to direct a larger number of potential patients to those practitioners who have demonstrated an ability to handle larger case loads and who have developed more skills and efficiencies in the new procedures.

For these reasons, it would be desirable to develop and implement new methods and procedures for referring patients to practitioners for performing novel and often proprietary medical procedures. Such methods and systems should provide referrals to most or all of the practitioners who have become certified to perform a new procedure but should preferentially direct referrals to those practitioners who are best able to handle a large number of patients. At least some of these objectives will be met by the inventions described hereinafter.

SUMMARY OF THE INVENTION The present invention provides methods and systems for referring patients to practitioners who perform medical procedures. The medical procedures will typically be new and innovative procedures which are being introduced into the medical community by a company, organization, or institution which has developed the procedure and which usually has proprietary rights to the procedure. In this way, the company, organization, or other institution can maintain control over performance of the procedure, typically by controlling training of the practitioners as well as by dispensing and distributing of the tools, devices, and kits required to perform the procedures. An exemplary procedure for referral according to the present invention is an orthodontic procedure which is performed using the Invisalign® System available from Align Technology, Inc., Santa Clara, Calif. The procedure as well as the appliances used in the procedure are proprietary and described in U.S. Pat. No. 5,975,893, as well as the following pending U.S. patent applications:

| | | | | |
|---|---|---|---|---|
| 09/466,353 | 09/298,268 | 09/454,786 | 09/454,278 | 09/483,071 |
| 09/169,276 | 09/169,036 | 09/169,034 | 09/313,291 | 09/264,547 |
| 09/313,290 | 09/311,941 | 09/311,716 | 09/311,715 | 09/539,185 |
| 09/539,021 | 09/534,461 | 60/199,485 | 60/199,662 | 60/199,663 |
| 60/199,610 | 60/199,465 | 09/616,222 | 09/506,419 | 09/560,052 |
| 09/557,382 | 09/566,424 | 09/576,721 | 09/621,716 | 09/620,253 |
| 09/626,192 | 09/641,208. | | | |

The disclosures of the issued patent, as well as all pending applications, are incorporated herein by reference.

In a first aspect of the present invention, a method for referring patients to practitioners comprises certifying a group of practitioners to perform a medical procedure, such as an orthodontic procedure. Individual patients who wish to receive the procedure are identified, and the identified patients are provided with a referral list of certified practitioners. In order to assure that most patients are referred to practitioners who have significant experience in performing the procedure, the list preferentially includes and/or presents practitioners who have performed more procedures than other practitioners. Typically, the practitioners will be placed into "tiers" or levels which reflect the number of procedures performed, with those practitioners who have performed more procedures being assigned to higher tiers while those who have performed fewer procedures are assigned to lower tiers. The ability to direct or channel patients to experienced practitioners has a number of advantages. The majority of patients will be seen by practitioners who have significant experience and who have probably gained additional skills. Conversely, by directing or channeling fewer referral patients to those practitioners with less experience, those practitioners can gain experience without becoming overwhelmed with referrals. Additionally, those practitioners who have decided to emphasize or focus their practice on the procedure will benefit from a continuing referral base of patients interested in having the procedure performed.

Certification of the practitioners may be as simple as registering those practitioners who have a desire to perform the procedure. More usually, however, the practitioners will undergo education and/or training prior to certification. Such training will typically be provided by the company, organization, or other institution which sponsors the procedure, typically in the form of formal training sessions (e.g., seminars), written materials, electronic teaching materials, and presentations by a sales force, and the like. In addition to training, certification may require that the practitioners be tested, and in some instances it may be desirable to require that the practitioners perform at least one procedure, usually with a previously certified practitioner or trainer present.

Once certified, the names, addresses, and other contact information (such as phone number, facsimile number, e-mail address, and the like) will be collected for the practitioner and maintained in a referral directory. The referral directory will be updated periodically with new practitioners being added as they become certified. Of course, practitioners can be removed from the referral directory as well. Practitioners may be removed at their request or by action of the company, organization, or institution which maintains the referral directory. For example, should for any reason it become apparent that the practitioner has in the past, or continues to perform the procedure in an unacceptable fashion, the practitioner's name may be removed from the referral directory. The referral directory will also be updated with respect to status. For example, as practitioners perform additional procedures, the tier or other status designation may be upgraded. In instances where the sponsoring company or organization distributes the product necessary to perform the procedure, the number of procedures performed by an individual practitioner can be updated based on the number of kits, tools, or other products ordered by the practitioner from the sponsoring organization.

The referral directory will be organized in a manner which facilitates providing referrals information to individual patients. In particular, the referral directory will allow the sorting and retrieval of practitioners practicing in a given geographic area to facilitate matching of practitioners with the locations of prospective patients. For example, the referral directory may allow identification of doctors based on their addresses, zip codes, or the like, where that information can be matched with similar information from the prospective patient. From the geographic information, in most instances at least, a significant number of practitioners could be identified for any particular prospective patient. According to the present invention, however, the practitioners who are closer to the patient will be further selected so that the experienced practitioners who have performed more procedures are preferentially included on a referral list which is eventually provided to the patient. Usually, the practitioners will be arranged into tiers or levels based upon the number of procedures that they have performed. Practitioners may be randomly ordered within a tier or may further be ranked in a tier, typically based on the number of procedures performed. Usually, each tier will be defined by a threshold of a number of procedures performed over a selected period of time. Alternatively, the threshold number may be the cumulative or aggregate number of procedures performed by the practitioner measured from the time they began performing the procedure.

Usually, there will be at least three tiers to which the practitioners will be assigned. For example, practitioners may be assigned to an initial or lowest tier when they first become certified. After performing a certain threshold number of procedures, typically in the range from 5 to 25 during a calendar quarter, for the exemplary use of the Invisalign® System, practitioners may be assigned to an intermediate or next higher tier. The third or highest tier would then be achieved when the practitioner has performed a still higher threshold number of procedures, typically in the range from 10 to 50 procedures during a calendar quarter. Of course, there could be fourth, fifth, and even higher tiers, each of which would have a still higher threshold number of procedures defining its entry level.

In a second aspect, methods according to the present invention for referring patients to dental practitioners comprise certifying the dental practitioners to perform a dental procedures, such as the orthodontic procedure using the Invisalign® System described above. The method further comprises informing a potential patient population of the availability of the procedure, typically through advertising in the print and electronic media. Individual patients who are identified are provided with a referral list of certified practitioners, where the practitioners are placed on the referral lists based on one or more performance criteria, typically including at least the number of procedures performed. The number of procedures performed may be determined over a preselected or fixed time period or alternatively may represent the cumulative or aggregate number of procedures performed by the practitioner. The certification process has generally been described above. The practitioners are preferentially placed on the referral lists typically utilizing a tiering approach as described above. Individual patients will usually contact a referral center either by telephone, e-mail, or other electronic communication system.

In a third aspect of the present invention, methods for referring patients to practitioners comprise maintaining a referral directory, soliciting and receiving inquiries from prospective patients, and referring to individual patients practitioners from the referral directory that are located within the patient's geographic area. As described previously, the listing of practitioners in the referral directory will usually be prioritized into a plurality of tiers, typically at least three, depending on the number of procedures that each practitioner has performed. Maintaining the referral directory comprises certifying practitioners to perform the procedure, tracking the number of times each certified practitioner performs the procedure to produce a performance number for that practitioner, and periodically updating the referral directory to reflect updated performance numbers. As before, the performance numbers can either be based on the cumulative or aggregate number of procedures performed, but will more usually be based on the number of procedures performed by an individual practitioner over a predetermined time interval.

Soliciting typically comprises advertising and providing contact information that permits a prospective patient to contact a referral center. The referral center may be staffed by people who answer telephones or respond to electronic communications or may be provided by an automated response system, such as a telephone or web-based system which allows a patient to navigate through the system using a series of menus and prompts. Referring will comprise first determining a patient's geographic area and then generating from the referral directory a referral list of practitioners within the patient's geographic area. Usually, the list will include a plurality of practitioners from the geographic area, where the practitioners are selected and/or arranged so that practitioners from the higher tiers are preferentially presented relative to practitioners from a lower tier. The preference can be that the practitioners from higher tiers are listed more frequently, i.e., on more referral lists, than practitioners from lower tiers. Alternatively or additionally, practitioners from higher tiers may be placed more prominently on a referral list, e.g., usually at the beginning of the list rather than near an end of the list. By providing such preferential listings, it is expected that the practitioners on higher tiers who have performed more procedures will be contacted by more prospective patients as a result of the referral process than will practitioners from lower tiers.

In other cases, referring may comprise determining the location of the patient's geographic area and then selecting a single practitioner to be referred to the patient. In that case, the practitioners from higher tiers will be selected more frequently than those from lower tiers, thus again causing the practitioners from higher tiers to receive more referral calls from prospective patients. With both of these approaches, however, it may be preferred that all practitioners included in the referral directory will receive at least some calls (although in some instances the practitioners in the lower tiers may only receive referrals when no practitioners from higher tiers are present in a patient's geographic area). It may be advantageous that the practitioners from the lower tiers receive referrals (although in lesser number or at a lower rate) to give them the opportunity to gain experience in the procedure with less likelihood that they will be overwhelmed with referrals and new patients desiring to have the procedure. Additionally, those practitioners in the lower tiers who choose to do so may make an effort to work with both the referred patients as well as patients from other referral sources in order to increase the number of procedures that they perform and are in a higher tier in which case they will receive more referrals.

In yet another aspect of the present invention, a computer system having a processor and memory for generating a list of medical practitioners for referring to potential patients comprises a means for maintaining a referral directory and a means for sorting practitioners on the referral directory to produce a referral list. The means for maintaining a referral directory will include contact information for practitioners who are certified to perform the procedure wherein the practitioners are prioritized in a plurality of tiers depending on the number of procedures that they have performed. The means for sorting produces a referral list in response to an inquiry from a prospective patient wherein practitioners are first selected based on proximity to the geographic area of the patient. The practitioners are further preferentially selected based on the tier to which the practitioner has been assigned. As described above, the referral list may include a plurality of practitioners where the practitioners from the higher tiers may be included more often (or in some cases exclusively) on lists and/or included more prominently on lists, i.e., placed higher on a list than a practitioner in the same area but from a lower tier. Alternatively, the referral list may include only a single practitioner, where practitioners from the same geographic areas but from higher tiers are included on more lists than those from lower tiers. A computer system will further comprise means for inputting data into the maintaining means and means for displaying the referral lists. In a specific example, the display means is a visual display means which is useful for human operators manning telephone call centers. The computer system may be used as a part of a web-based system for automatically producing referral lists for prospective patients who choose to contact he provider over the web.

DESCRIPTION OF THE SPECIFIC EMBODIMENTS

The present invention for selecting and referring prospective patients to practitioners to will be described with respect to a method and system for orthodontics as described in U.S. Pat. No. 5,975,893, the full text of which has been previously incorporated herein by reference. The methods and systems described in that patent are now commercially available under the Invisalign® System trade name from Align Technology, Inc., Santa Clara, Calif. Briefly, certified orthodontic practitioners obtain an impression of the patient's teeth, usually both upper and lower jaws, which is then scanned or otherwise processed to produce a digital data set representing the initial position of the teeth. From that data set, Align Technology generates a final data set representing a desired tooth configuration which is based upon a prescription received from the orthodontic practitioner. After confirming the final tooth arrangement with the orthodontic practitioner, Align then models and produces a plurality of aligners which are polymeric shells which may be placed upon the teeth. Each of the successive aligners has a slightly different geometry selected to move the teeth toward their desired final positions. From between 20 and 60 aligners are normally used in any single course of treatment. The Invisalign® System is proprietary, and Align Technology certifies orthodontic practitioners to practice using the system. Align Technology will distribute and dispense the Invisalign®System only through those orthodontic practitioners who have been certified by Align to perform the procedure. While the present invention will be described with respect to the Invisalign® System, it will be appreciated that the methods and systems of the present invention will be useful with a variety of other medical procedures and systems where a company, organization, or other institution is in a position to certify practitioners and/or control the distribution and dispensing of the system to the practitioners.

Figure 1:
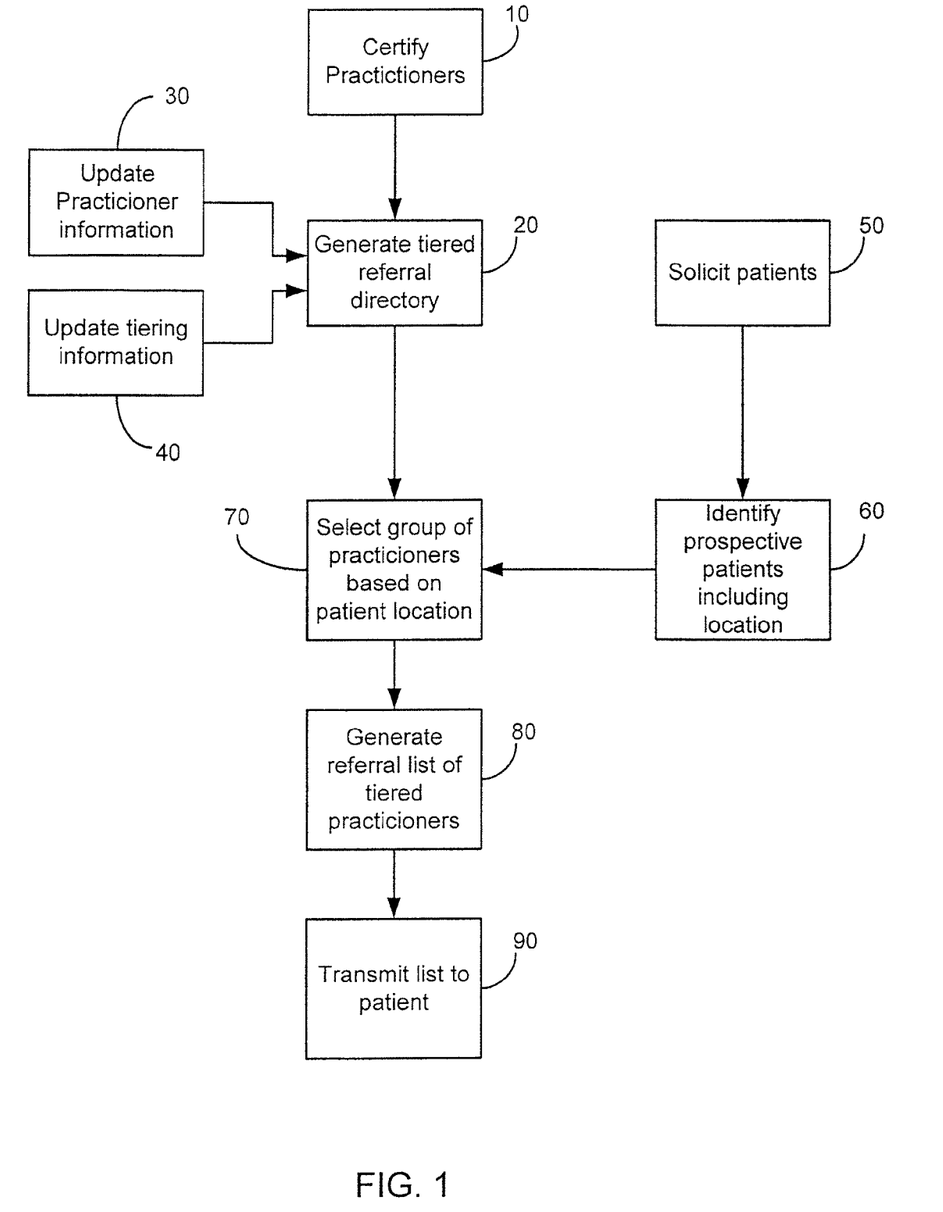
FIG. 1 is a block diagram illustrating the flow of information in the methods and systems of the present invention.

Referring now to FIG. 1, the present invention begins with the certification of practitioners as indicated at box 10. The practitioners will usually be orthodontists and the certification process will usually require attendance by the practitioner at a course where the details of the procedure are taught. Certification, however, could require more, e.g., testing, performance of at least one procedure under the guidance of a previously certified practitioner or teacher, or the like. Alternatively, certification could require mere registration if the procedure involved were not particularly complex and did not require specific training. As described elsewhere, however, the present method and system are particularly useful for relatively complex procedures which required training.

Once an initial group of practitioners has been certified, identification and contact information from each of the certified practitioners may be collected into a referral directory. The referral directory will usually be maintained as part of an electronic data base, permitting relatively easy access, updating, and manipulation, as described in more detail below. The referral directory will be updated as additional practitioners are certified and as practitioners are removed, if for any reason that should be necessary. Performance criteria, e.g., numbers of procedures and/or tiering, will also be updated over time as the practitioners gain experience.

The methods of the present invention rely on the preferential referral of certified practitioners based on a performance criteria, typically the number of procedures that that practitioner has performed. For all the reasons discussed above, it is believed that referring the greatest number of patients to practitioners who have the most experience and are likely the most efficient will be beneficial both to the patient and to the practitioner. Once the referral directory has been generated, such preferential referrals to patients can be effected in a variety of ways. Most simply, the referral directory could include the number of procedures which have been performed by an individual practitioner to date or over a specified prior period. More referrals could then be given to the practitioners who have achieved higher performance numbers than those who have achieved lower performance numbers. Usually, however, it will be more manageable to create "tiers" or levels within the referral directory, as shown in block 20. Successively higher tiers can be achieved as any practitioner completes certain threshold numbers of cases. For example, for practice with the Invisalign® System, an initial tier would include those practitioners who have been certified but who have completed fewer than a first threshold number of cases, usually in the range from 5 cases to 25 cases during a calendar quarter. Alternatively, the first threshold number could be a cumulative or aggregate number, typically in the range from 25 cases to 100 cases. Once a practitioner has exceeded this first threshold number of cases, the practitioner will enter the second tier, where that practitioner will remain until completing a second threshold number of cases. For the Invisalign® System, the second threshold will typically be from 10 cases to 50 cases over a calendar quarter, or from 50 cases to 200 cases measured cumulatively. After exceeding the second threshold number, the practitioner will be in the third or highest tier. Of course, any number of additional tiers could be created if there is a reason to do so.

While the above three-tiered scheme is particularly suitable for referring doctors using the Invisalign® System, the protocols can vary widely for other dental and medical procedures. For example, in some instances, it may be desirable to tier or grade the doctors based on some objective or subjective measure of their ability. For example, doctors who have been recognized as being particularly skilled in performing the subject procedure can be placed in higher tiers compared to doctors who are just beginning to learn the procedure. In other instances, it may be appropriate to tier doctors, at least in part, based on an individual doctor's expressed desire to perform more or fewer procedures. Additionally, in some instances, it may be desirable to tier doctors based on the availability of specialized equipment to perform the procedure and/or the size or availability of staff or other support to assist the doctor in performing the procedures. Of course, any two or more of these particular criteria can be combined and considered in assigning a doctor to a tier or level within the patient referral methods of the present invention.

The tiered referral directory, shown in block 20, will not be a static listing. Instead, it will be up-dateable to permit the addition of practitioners as well as the updating of individual practitioner information (block 30), such as new addresses, telephone numbers, web addresses, or the like. The tiered referral directory will also be updated as individual practitioners complete additional cases and move upward through the tiered levels (block 40).

The methods of the present invention also rely on soliciting patients (block 50), at least some of whom are subsequently referred to practitioners listed in the tier referral directory. A patient's solicitation will be through print or electronic advertising where the patients will be invited to contact a referral center. The referral center will usually have human operators who can answer telephone inquiries, e-mail inquiries, and the like. Alternatively, the referral center could comprise an automated response system which would reply to telephone inquiries based on a prerecorded menu and prompt system or could simply reply to internet or e-mail inquiries in an automated fashion. In addition to providing information to prospective patients, the referral center will obtain contact information from those prospective patients who express a desire to either receive general information or more specifically to receive a referral list including certified practitioners in their geographic area (block 60). Thus, it will be necessary to obtain information concerning the patient's location. Typically, an address or just a zip code of either the either the patient's home address or work address will be sufficient (although it may be necessary to get a postal or electronic address to send lists and/or other information).

The present invention will select practitioners based on the patient's location (block 70) and will generate a referral list of certified practitioners for those prospective patients who desire one. The referral list first identifies a group of practitioners who practice within a reasonable distance of the patient's location. Usually, this can be determined based upon zip code. Once the group of conveniently located practitioners has been generated, typically but not necessarily including all certified practitioners within a reasonable distance of the patient, the present invention will preferentially select among those practitioners to produce the referral list (block 80).

Usually, the referral list will include a plurality of practitioners, typically from one to 25, or typically from three to 15. If fewer than the target number of practitioners are present within a reasonable distance of the patient, then the referral list can simply include all practitioners who are within a requisite distance from the patient. Assuming, however, that more practitioners are close to the patient than are to be included on the referral list, it becomes necessary to select practitioners for the referral list for that individual patient.

Exemplary rules that can be applied to practitioner selection are as follows. A computer system which maintains the referral list can be programmed to receive locational information, such as address or zip code, of a prospective patient. Based on that locational information, the computer can select and order practitioners based on the following rules. First, all of the highest-tiered doctors who are closest to the patient, e.g., within five miles, can be retrieved from the list. Next, all of the highest-tiered doctors located within a next distance range from the patient, e.g., five to ten miles can be retrieved. Then, all of the next highest-tiered doctors within some distance from the patient can be selected, e.g., within ten miles. Then all of the highest-tiered doctors within some further distance from the patient, e.g., from 10 to 20 miles can be selected. Next, all of the second highest-tiered doctors within a similar range, e.g., 10 to 20 miles can also be selected. The selection of practitioners could continue but usually will be terminated after a target number has been reached, e.g., from three to 25, usually five to 10. Each of the retrieved groups of doctors can then be presented in a listing in order. Usually, doctors within each grouping, e.g., the highest-tiered doctors who are closest to the patient, will be randomly ordered and/or the order will be chosen so that the same doctors will not always appear first on the list provided to the patient. Similar randomization and/or selection of the doctors in each of the subsequent groupings will also take place.

Additional rules which may be employed and generating the patient referral lists include the following. First, there will usually be a maximum number of doctors generated for any particular patient, e.g., 15. This number, of course, can vary widely. If the search protocol described above fails to identify any doctors, or fails to identify an adequate number of doctors, then lower-tiered doctors within some preselected distance of the patient can then be provided on or added to the patient referral list. Optionally, the search can be stopped at some maximum distance from the patient's location, e.g., 200 miles. This practitioner selection protocol can be used both in fully automated systems, e.g., automated responses to inquires made over the company's website, or may be provided on computer screens which permit human operators to give information to prospective patients over the phone. Of course, the information could be provided via e-mail, facsimile, or other electronic means if desired. Additionally, both the human-operated and automatic website systems will usually allow prospective patients to search for practitioners by name to determine both their locations and whether they have been certified to perform the procedure.

After the referral list is generated, as shown in block 80, the list will be transmitted to the patient (block 90). If the patient has telephoned a call center, a list will usually be presented to an operator on a screen and may be simply read to the patient. In other instances, the list may be transmitted electronically, typically via e-mail, faxed, or sent by regular mail. The referral list will usually include at a minimum, the name of the practitioner, as well as address and contact information, such as telephone number, e-mail address, or the like.

Figure 2:
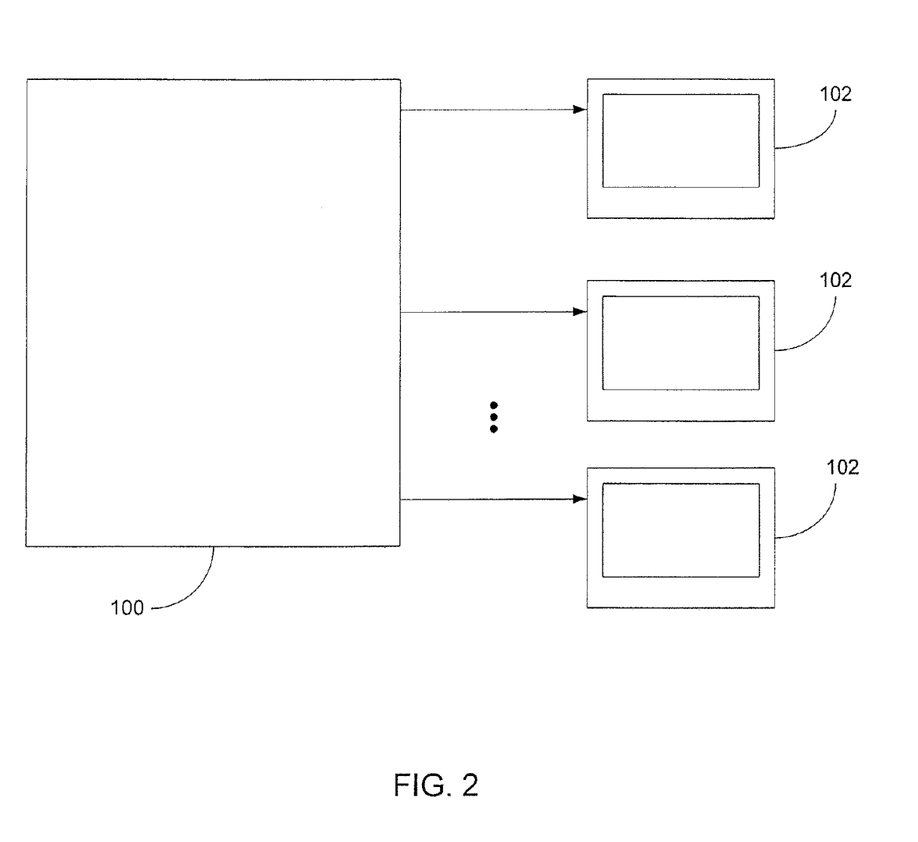
FIG. 2 is a schematic illustration of a computer system adapted for practicing the methods of the present invention.

Referring now to FIG. 2, systems according to the present invention will comprise a computer 100 which is typically networked to a plurality of remote computers or monitors 102. The computer will include normal hardware such as a processor, internal memory, input devices, such as an internal hard disc, external floppy disc, CD-ROM, and the like, typically being a networked system where computer 100 may comprise a server and computers/monitor 102 are connected to the server using conventional networking software.

The computer will be adapted to store the referral directory of certified practitioners. The computer will still further be adapted to permit updating of the referral directory from time to time, both to add new certified practitioners and to update and change the tiering information of the practitioners. The computer will still further be adapted to generate referral lists of the tier practitioners in response to inquiries, such as the input of patient locations. In such instances, the compute will apply the selection rules described above.

Figure 3:
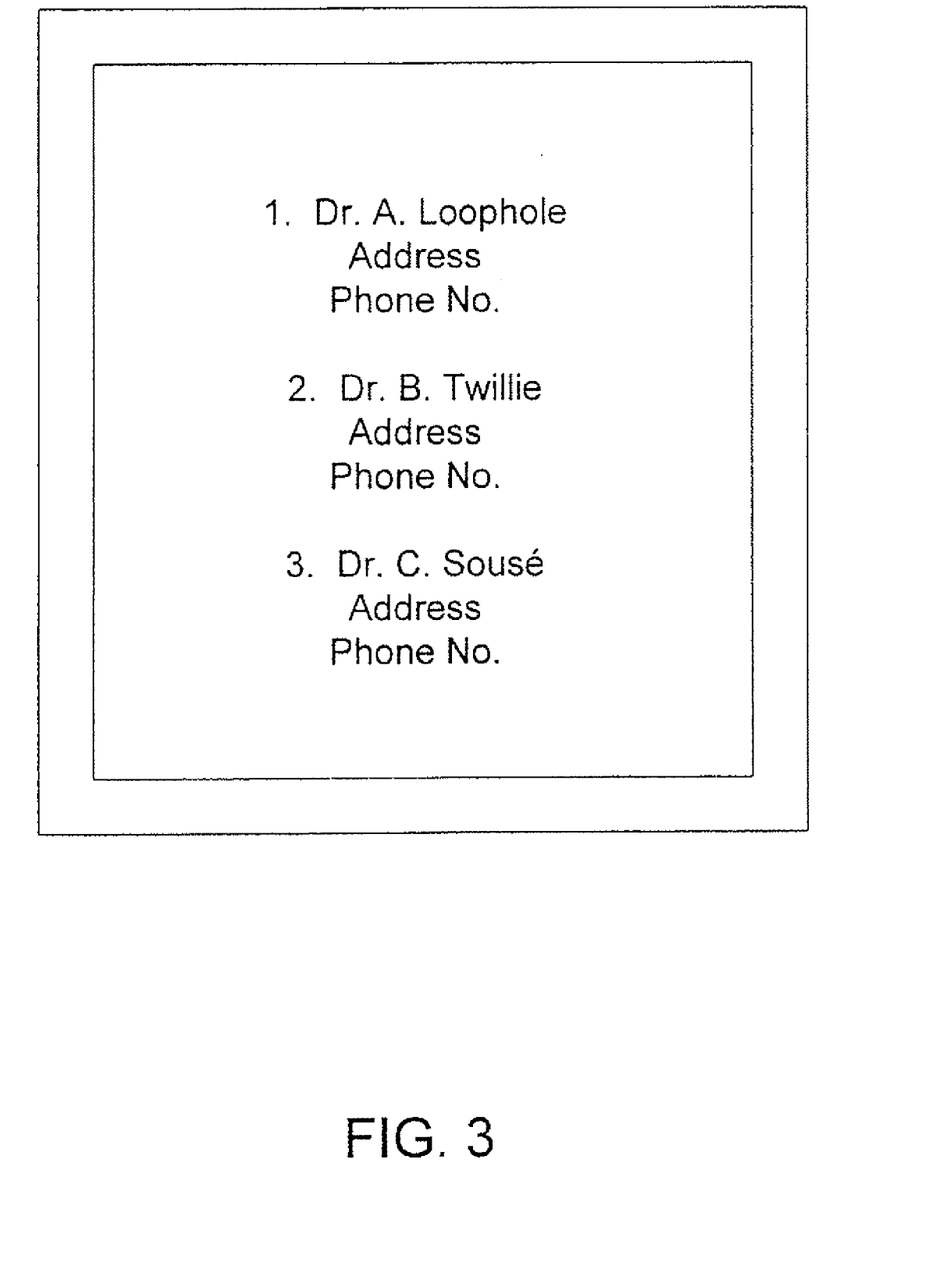
FIG. 3 illustrates a referral list generated in accordance with the principles of the present invention as it might be shown on a visual monitor of the computer system of FIG. 2.

In use, an operator at one of the monitors 102 will receive an inquiry and input prospective patient information, including the patient location, typically at least a zip code. Based on the location information, the computer 100 will generate an ordered list of certified practitioners, as shown in FIG. 3. The operator may then verbally provide the information relating to the referral list to a patient, either over the phone, via e-mail, via facsimile, or by other suitable transmission means.

In other instances, of course, the computer may be adapted to communicate directly with prospective patients, either via the web or via an automated telephone system.

In both cases, there will be no need to provide individual monitors for operators receiving calls. Instead the computer will receive an electronic inquiry in the form of menus and prompts and provide an automated response. For web-based systems, the response will usually be a direct response to the inquiring patient over the web during the session initiated by the patient. For automated telephone systems, the reply will typically be via synthesized speech. In both cases, the responses could be confirmed and/or additional information provided by mail or facsimile. Both mail and facsimile responses can be automated based on the information received electronically from the prospective patient.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for referring patients to practitioners to perform a procedure, said method comprising:
   maintaining a referral directory comprising data stored on a computer system, the referral directory data including contact information for practitioners and information that the practitioners, are certified to perform the procedure, the data further comprising information for sorting practitioners prioritized in a plurality of tiers depending on the number of procedures that they have performed;
   electronically receiving inquiries from prospective patients regarding the procedure; and
   electronically transmitting a referral to individual patients, in response to their requests, practitioners within the patient's geographic area, wherein practitioners are selected from the referral directory and sorted by the computer system such that the transmitted referral preferentially presents practitioners from tiers which require a higher number of procedures relative to practitioners from tiers which require a lower threshold number of procedures.

2. A method as in claim 1, wherein maintaining the referral directory comprises:
   certifying practitioners to perform the procedure;
   tracking the number of times each certified practitioner performs the procedure to produce a performance number for each practitioner; and
   periodically updating the referral directory to reflect updated performance numbers.

3. A method as in claim 2, wherein the performance number comprises the aggregate number of procedures performed by an individual practitioner.

4. A method as in claim 2, wherein the performance number comprises the number of procedures performed by an individual practitioner over a predetermined time interval.

5. A method as in claim 1, wherein the plurality of tiers is at least three.

6. A method as in claim 1, wherein the method further comprises soliciting patients, the soliciting comprising advertising and providing contact information that permits a patient to contact a referral center.

7. A method as in claim 6, wherein the referral center comprises a person.

8. A method as in claim 6, wherein the referral center comprises an automated response system.

9. A method as in claim 1, wherein referring comprises:
   determining the location of the patient's geographic area; and
   generating from the referral directory a referral list of practitioners within the patient's geographic area, wherein the list includes a number of practitioners selected and/or arranged so that practitioners from higher tiers are preferentially referred.

10. A method as in claim 9, wherein the higher tiered practitioners are placed on lists in any geographic area more often than lower tiered practitioners.

11. A method as in claim 9, wherein the higher tiered practitioners are placed earlier on a single list than the lower tiered practitioners.

12. A method as in claim 1 wherein referring comprises:
    determining the location of the patient's geographic area; and
    selecting a single practitioner to be referred to the patient, wherein practitioners from higher tiers are selected more often than those from lower tiers.

13. A method as in claim 9 or 12, wherein all practitioners are included on at least some referral lists.

14. A method as in claim 1, wherein the referral directory comprises an electronic database, wherein soliciting comprises receiving voice or data inquiries from potential patients at a central location, and wherein referring comprises generating a referral list from the electronic database and responding to the inquiry by providing the referral list to the patient.

15. A method as in claim 14, wherein generating the referral list comprises presenting an ordered list of practitioners on a display screen and responding comprises reading at least some of the names of the practitioners to the potential patients.

16. A computer system for generating a list of medical practitioners, for referring to potential patients, said system comprising:
- an electronic database maintaining a referral directory which includes data comprising contact information for practitioners who are certified to perform a procedure, wherein the data comprises information allowing sorting of the practitioners prioritized in a plurality of tiers depending on the number of procedures that they have performed; and
- computer-readable instructions which, when executed by a computer, sort practitioners of the referral directory to produce a referral list in response to an inquiry from a prospective patient in a particular geographic location wherein practitioners are first sorted into tiers based on proximity to the geographic location and then sorted within each tier to which the practitioner has been assigned based on the number of procedures that they have performed.

17. A computer system as in claim 16, wherein the electronic database is updateable to add and remove practitioners and to change the tier status of individual practitioners.

18. A computer system as in claim 16 or 17, wherein the electronic database includes at least three tiers with practitioners who have performed more than a first threshold number of procedures being in a higher tier, those who have performed more than a second threshold number but less than the first threshold number being in a lower tier, and those who have performed less than the second threshold number being in a still lower tier.

19. A computer system as in claim 18, wherein the number of times the procedure is performed is measured over a fixed time interval.

20. A computer system as in claim 18, wherein the number of times the procedure is performed is cumulative.

21. A computer system as in claim 16, wherein the practitioners are not ordered within a tier.

22. A computer system as in claim 16, wherein the practitioners are further ranked within each tier based on the number of procedures performed.

23. A computer system as in claim 16, wherein the means for sorting will select a plurality of practitioners for each referral list with at least practitioners from the highest tier being selected most often, those from the lower tier being selected less often, and those from the still lower tier being selected still less often.

24. A computer system as in claim 16, wherein only a single practitioner is selected for each referral list, with at least practitioners from the highest tier being selected most often, those from the lower tier being selected less often, and those from the still lower tier being selected still less often.

25. A computer system as in claim 16, wherein all practitioners are selected at least some of the time.

26. A computer system as in claim 16, further comprising a computer for inputting data into the electronic database and a display for displaying the referral lists.

* * * * *